United States Patent [19]

Tessier et al.

[11] Patent Number: 4,618,364
[45] Date of Patent: Oct. 21, 1986

[54] 3-(2-TETRAHYDROPYRANYL)-1,2,3,4,5,6,7-HEXAHYDRO-1-P-TOLYLOXYCARBONYL-5H-CYCLOPENTAPYRIMIDINE-2,4-DIONE AND HERBICIDAL COMPOSITIONS AND METHODS USING IT

[75] Inventors: Jean Tessier, Vincennes; Pierre Girault, Paris, both of France

[73] Assignee: Roussel Uclaf, Paris, France

[21] Appl. No.: 628,331

[22] Filed: Jul. 6, 1984

[30] Foreign Application Priority Data

Jul. 11, 1983 [FR] France ................................ 83 11518

[51] Int. Cl.⁴ ................... A01N 47/38; C07D 239/70
[52] U.S. Cl. ......................................... 71/92; 544/253
[58] Field of Search ............................. 544/253; 71/92

[56] References Cited
U.S. PATENT DOCUMENTS 3,920,653 11/1975 Wenzelburger et al. ....... 544/253 X

FOREIGN PATENT DOCUMENTS 0060955 9/1982 European Pat. Off. .
2468603 5/1981 France .
1257259 12/1971 United Kingdom .

Primary Examiner—Donald G. Daus
Assistant Examiner—Diana G. Rivers
Attorney, Agent, or Firm—Bierman, Peroff and Muserlian

[57] ABSTRACT

Novel uracils of the formula

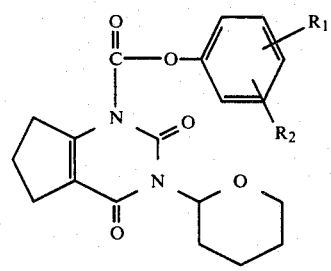

wherein $R_1$ is selected from the group consisting of alkyl of 1 to 8 carbon atoms, alkoxy of 1 to 8 carbon atoms, halogen and —C(Hal)$_3$, Hal is halogen and $R_2$ is hydrogen or $R_1$ and $R_2$ taken together with the benzene ring to which they are attached form a system of two coupled rings optionally containing at least one heteroatom having selective herbicidal activity.

6 Claims, No Drawings

3-(2-TETRAHYDROPYRANYL)-1,2,3,4,5,6,7-HEXAHYDRO-1-P-TOLYLOXYCARBONYL-5H-CYCLOPENTAPYRIMIDINE-2,4-DIONE AND HERBICIDAL COMPOSITIONS AND METHODS USING IT

STATE OF THE ART

French patent No. 2,468,603 describes uracils of the formula

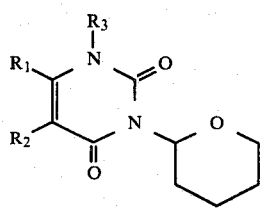

wherein $R_1$ and $R_2$ are alkyl or together with the carbon atoms t which they are attached form a carbon homocycle or a thiophene and $R_3$ is —COOZ and Z is selected from the group consisting of alkyl, cycloalkyl, phenyl and benzyl but no substituted phenyls U.S. Pat. No. 3,732,228 also describes compounds close to the uracils of the invention. The said compounds have a non-selective herbicidal activity.

OBJECTS OF THE INVENTION

It is an object of the invention to provide the novel uracils of formula I and to provide a novel process for their preparation.

It is another object of the invention t provide selective herbicidal compositions and to provide a novel method of selectively killing weeds.

These and other objects and advantages of the invention will become obvious from the following detailed description.

THE INVENTION

The novel compounds of the invention are uracils of the formula

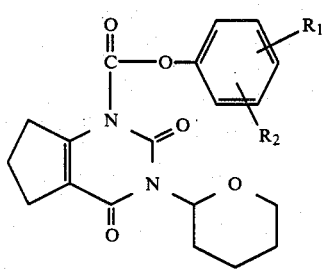

wherein $R_1$ is selected from the group consisting of alkyl of 1 to 8 carbon atoms, alkoxy of 1 to 8 carbon atoms, halogen and —C(Hal)$_3$, Hal is halogen and $R_2$ is hydrogen or $R_1$ and $R_2$ taken together with the benzene ring to which they are attached form a system of two coupled rings optionally containing at least one heteroatom.

Examples of $R_1$ are alkyl of 1 to 8 carbon atoms such as methyl, ethyl, propyl, isopropyl, and linear or branched butyl, pentyl, hexyl, heptyl and octyl; halogens such as fluorine, chlorine and bromine; alkoxy of 1 to 8 carbon atoms such as methoxy, ethoxy, propoxy, isopropoxy and linear and branched butoxy, pentoxy, hexyloxy, heptyloxy and octyloxy; and —C(Hal)$_3$ such as —CF$_3$, —CCl$_3$ and —CBr$_3$. Examples of the two ring system with $R_1$ and $R_2$ together with the phenyl group are naphthalene, benzofuran, benzothiophene, benzylazole, benzothiazole, 1,4-chromene and quinazoline. Especially preferred are the compounds where $R_2$ is hydrogen.

Examples of specific compounds of formula I are 3-(2-tetrahydropyranyl)-1,2,3,4,6,7-hexahydro-1-p-tolyloxy-carbonyl-5H-cyclopentapyrimidine-2,4-dione; 3-(2-tetrahydropyranyl)-1,2,3,4,6,7-hexahydro-1-(3-trifluoromethylphenoxycarbonyl)-5H-cyclopentapyrimidine-2,4-dione; 3-(2-tetrahydropyranyl)-1,2,3,4,6,7-hexahydro-1-(4-tert-butylphenoxycarbonyl)-5H-cyclopentapyrimidine-2,4-dione; 3-(2-tetrahydropyranyl)-1,2,3,4,6,7-hexahydro-1-(3-methyl-phenoxycarbonyl)-5H-cyclopentapyrimidine-2,4-dione; 3-(2-tetrahydropyranyl)-1,2,3,4,6,7-hexahydro-1-(2-methyl phenoxycarbonyl)-5H-cyclopentapyrimidine-2,4-dione; 3-(2-tetrahydropyranyl)-1,2,3,4,6,7-hexahydro-1-(α-naphthyloxycarbonyl)-5H-cyclopentapyrimidine-2,4-dione; 3-(2-tetrahydropyranyl)-1,2,3,4,6,7-hexahydro-1-(4-chlorophenoxycarbonyl)-5H-cyclopentapyrimidine-2,4-dione; 3-(2-tetrahydropyranyl)-1,2,3,4,6,7-hexahydro-1-(4-methoxyphenoxycarbonyl)-5H-cyclopentapyrimidine-2,4-dione.

The novel process for the preparation of the compounds of formula I comprises reacting 3-(2-tetrahydropyranyl)-1,2,3,4,6,7-hexahydro-5H-cyclopentapyrimidine-2,4-dione described in French Pat. No. 2,029,250 with a strong base and then with a compound of the formula

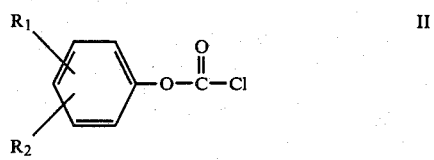

wherein $R_1$ and $R_2$ have the above definition to form the corresponding compound of formula I. The preferred strong base is preferably an alkali metal hydride such as sodium hydride.

The novel selective herbicidal compositions of the invention are comprised of an herbicidally effective amount of at least one compound of formula I and an inert carrier. The compositions may be in the form of powders, granules, suspension emulsions and solutions containing the active ingredient and optionally other pesticides and compounds which influence the plant growth.

Examples of suitable compositions are the active ingredient with a vehicle and/or an anionic, cationic or non-ionic surface active agent to ensure a uniform dispersion of the components in the composition. The vehicle may be a liquid such as water, alcohol, hydrocarbons, other organic solvents and mineral, animal or vegetable oil or a solid such as talc, clays, silicates or Kieselguhr.

The solid composition in the form of powders, wettable powders or granules may be prepared by grinding the active compound with an inert solid or by impregnation of a solid support with a solution of the active ingredient in a solvent which is subsequently evaporated. The compositions may contain 10 to 80%, preferably 10 to 50% by weight of the active material.

In contrast to the compounds of French Pat. No. 2,468,603 which are devoid of selective herbicidal activity on rice, the compositions of the invention show selective herbicidal activity against weeds in rice, cotton and corn crops. The selective herbicidal activity has been demonstrated by tests on plant respresentative of large botanical families such as wheat, barley, corn, wild oats, agrostis, lolium, vulpin, Panicum crusgalli, rice, beetroot, chenopodium, chrysanthemum, cleavers, soya, cotton, mustard, amaranthus, xanthium.

The novel method of selectively killing weeds comprises contacting weeds in a useful crop with an herbicidally effective amount of at least one compound of formula I. The active compounds may be applied pre- or post-emergence. The preferred useful crops are rice, cotton and corn, especially rice.

The active compounds are applied in quantities sufficient to exercise their herbicidal activities and the quantities of active material in the compositions vary depending particularly on the vegetation to be destroyed, on the nature of the soil, the atmospheric conditions and the state of advancement of the vegetation to be destroyed. Generally, the quantities of active material applied vary in pre-emergence preferably between 0.1 and 5 kg/hectare and in post-emergence, preferably between 0.1 and 800 g/hectare.

In the following examples there are described several preferred embodiment to illustrate the invention. However, it should be understood that the invention is not intended to be limited to the specific embodiments.

EXAMPLE 1

3-(2-tetrahydropyranyl)-1,2,3,4,6,7-hexahydro-1-(p-tolyloxycarbonyl)-5H-cyclopentapyrimidine-2,4-dione 15 g of 3-(2-tetrahydropyranyl)-1,2,3,4,6,7-hexahydro-5H-cyclopentapyrimidine-2,4-dione [prepared according to the French Pat. No. 2,029,250] were introduced with stirring over 20 minutes at 20° C. into 130 ml of anhydrous tetrahydrofuran and 13 ml of hexamethylphosphotriamide and then 3.35 g of a 50% suspension of sodium hydride in oil were introduced in several portions at 0° C. with stirring for 105 minutes. Then 13 g of p-tolyl chloroformate prepared from p-cresol were introduced dropwise with stirring at 20° C. over 17 hours and the mixture was then poured into iced water. Isopropyl ether was added thereto and the mixture was vacuum filtered. The solid product was dried to obtain 15.5 g of 3-(2-tetrahydropyranyl)-1,2,3,4,6,7-hexahydro-1-(p-tolyloxycarbonyl)-5H-cyclopentapyrimidine-2,4-dione melting at 136° C.

EXAMPLE 2

3-(2-tetrahydropyranyl)-1,2,3,4,6,7-hexahydro-1(3-trifluoromethylphenoxycarbonyl)-5H-cycloentapyrimidine-2,4-dione Using the procedure of Example 1, 3-trifluoromethylphenyl chloroformate prepared from 3-trifluoromethylphenol was reacted to obtain 3-(2-tetrahydropyranyl)-1,2,3,4,6,7-hexahydro-1-(3-trifluoromethylphenoxycarbonyl)-5H-cyclopentapyrimidine-2,4-dione melting at 130° C.

EXAMPLE 3

3-(2-tetrahydropyranyl)-1,2,3,4,6,7-hexahydro-1-(4-tertbutylphenoxycarbonyl)-5H-cyclopentapyrimidine-2,4-dione Using the procedure of Example 1, 4-tert-butylphenyl chloroformate prepared from 4-tert-butylphenol was reacted to obtain 3-(2-tetrahydropyranyl)-1,2,3,4,6,7-hexahydro-1-(4-tert-butylphenoxycarbonyl)-5H-cyclopentapyrimidine-2,4-dione melting at 135° C.

EXAMPLE 4

3-(2-tetrahydropyranyl)-1,2,3,4,6,7-hexahydro-1-(3-methylphenoxycarbonyl)-5H-cyclopentapyrimidine-2,4-dione Using the procedure of Example 1, m-tolyl chloroformate prepared from m-cresol was reacted to obtain 3-(2-tetrahydropyranyl)-1,2,3,4,6,7-hexahydro-1-(3-methylphenoxycarbonyl)-5H-cyclopentapyrimidine-2,4-dione melting at 155° C.

EXAMPLE 5

3-(2-tetrahydropyranyl)-1,2,3,4,6,7-hexahydro-1-(2-methylphenoxycarbonyl)-5H-cyclopentapyrimidine-2,4-dione Using the procedure of Example 1, 0-tolyl chloroformate prepared from 0-cresol was reacted to obtain 3-(2-tetrahydropyranyl)-1,2,3,4,6,7-hexahydro-1-(2-methylphenoxycarbonyl)-5H-cyclopentapyrimidine-2,4-dione.

NMR Spectrum (deuterochloroform):
Peaks at 1.5 to 3.16 ppm

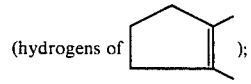

at 1.5 to 3.16 ppm

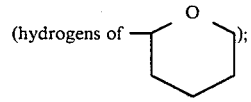

at 2.31 ppm (hydrogens of ortho-tolyl methyl); at 3.3 to 4.3 ppm

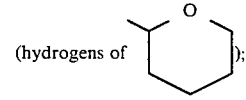

at 5.85–5.88 and 6.03–6.07 ppm

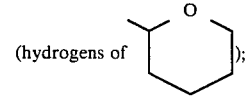

at 7.23 ppm (aromatic hydrogens).

EXAMPLE 6

3-(2-tetrahydropyranyl)-1,2,3,4,6,7-hexahydro-1-(α-naphthyloxycarbonyl)-5H-cyclopentapyrimidine-2,4-dione Using the procedure of Example 1, naphthyl chloroformate prepared as in J.A.C.S (1925) Vol 47, 2609 was reacted to obtain 3-(2-tetrahydropyranyl)-1,2,3,4,6,7-hexahydro-1-(α-napthyloxycarbonyl)-5H-cyclopentapyrimidine-2,4-dione melting at 160° C.

EXAMPLE 7

3-(2-tetrahydropyranyl)-1,2,3,4,6,7-hexahydro-1-(4-chlorophenoxycarbonyl)-5H-cyclopentapyrimidine-2,4-dione Using the procedure of Example 1, 4-chlorophenyl chloroformate prepared as in J.A.C.S. Vol. 47 2609 (1925) was reacted to obtain 3-(2-tetrahydropyranyl)-1,2,3,4,6,7-hexahydro-1-(4-chlorophenoxycarbonyl)-5H-cyclopentapyrimidine-2,4-dione melting at 126° C.

EXAMPLE 8

3-(2-tetrahydropyranyl)-1,2,3,4,6,7-hexahydro-1-(4-methoxyphenoxcarbonyl)-5H-cyclopentapyrimidine-2,4-dione Using the procedure of Example 1, 4-methoxyphenyl chloroformate prepared from 4-methoxyphenol was reacted to obtain 3-(2-tetrahydropyranyl)-1,2,3,4,6,7-hexahydro-1-(4-methoxyphenoxcarbonyl)-5H-cyclopentapyrimidine-2,4-dione melting at 110° C.

EXAMPLE 9

Emulsifiable concentrate

A composition was prepared containing 15% by weight of the product of Example 1, 6.4% of Atlox 4851 (oxyethylene triglyceride combined with a sulfonate, acidity index 1.5), 3.2% of Atlox 4855 (oxyethylene triglyceride combined with a sulfonate, acidity index 3) and 75.4% of xylene.

EXAMPLE 10

Wettable powder

A wettable powder was prepared containing 25% of the compound of Example 4, 15% of Ekapersol (condensation product of naphthalene sodium sulfonate), 0.5% of Brecolane NVA (alkyl naphthalene sodium sulfonate), 34.5% of Zeozil 39 (synthetic hydrated silica obtained by precipitation) and 25% of Vercoryl "S" (colloidal kaolin).

HERBICIDAL DATA

Pre-emergence herbicidal activity

The plants used were Triticum sativum, Hordeum sp., Zea mays, Avena ludoviciana, Agrostis tenuis, Lolium perenne, Alopecurus myosuroides, Panicum crusgalli, Oryza sativa, Beta vulgaris, Chenopodium album, Chrysanthemum coronarium, Galium aparine, Glycine hispida, Gosspyium spp., Brassica sp., Amarantus retroflexus, Xanthium spinosum and were cultivated in culture troughs (23×14×4 cm) with a double bottom with a provision for watering from below. The species were placed at the rate of 20 seeds per species, in rows spaced 3 cm apart in separate troughs, and there are 4 trials for each concentration. The cultivation conditions were as follows: temperature:20° C. ±2° C., humidity —about 60% lighting —by fluorescent tube (daylight+brilliant white) for 06.00 hours to 22.00 hours every day. The soil mixture was composed of 10 volumes of plain soil, 10 volumes of river sand and 2 volumes of peat.

A pre-emergence test was carried out when the treatment was applied twenty-four hours after sowing and the first watering was effected by spraying so as to draw a part of the product to the level of the seeds. The product under test was applied under standard conditions with a micro-atomizer at quantities corresponding to 2.5, 1.25 and 0.625 kg/hectare at a dilution corresponding to 560 l./hectare. A test was done with an untreated control which test used the same number of plantlets as those treated. The final check is done by counting the number of plantlets twenty-one days after treatment.

The results are expressed as a percentage of the reduction of the number of plants (mortality percentage)M:

$$M = \frac{\text{Number of control plantlets} - \text{Number of surviving treated plantlets}}{\text{Number of control plantlets}} \times 100$$

The experiamental results obtained with the compounds of Example 1 are summarized in the following table:

| Plants treated | Mortality percentage, Dose in kg/hectare. | | |
|---|---|---|---|
| | 2.5 | 1.25 | 0.625 |
| Triticum sativum | 100 | 17 | 50 |
| Hordeum sp. | 100 | 100 | 100 |
| Zea mays | 0 | 0 | 0 |
| Avena ludoviciana | 100 | 63 | 25 |
| Agrostis tenuis | 100 | 100 | 100 |
| Lolium perenne | 90 | 80 | 63 |
| Alopecurus myosuroides | 100 | 100 | 100 |
| Panicum crusgalli | 50 | 32 | 14 |
| Oryza sativa | 0 | 0 | 0 |
| Beta Vulgaris | 100 | 86 | 43 |
| Chenopodium album | 100 | 100 | 100 |
| Chrysanthemum coronarium | 100 | 79 | 39 |
| Galium aparine | 100 | 100 | 85 |
| Glycine hispida | 100 | 92 | 42 |
| Gossypium spp. | 0 | 0 | 0 |
| Brassica sp. | 100 | 100 | 100 |
| Amarantus retroflexus | 61 | 55 | 18 |
| Xanthium spinosum | 100 | 67 | 33 |

CONCLUSION

These experimental results show the good herbicidal selectivity of the compound of Example 1 on rice, cotton and corn.

Comparative study of pre-emergence herbicidal activity on rice of the compound of Example 1 (compound A) and 1-(methoxycarbonyl)-3-(2-tetrahydropyranyl)-5-ethyl-6-methyl-1,2,3,4-tetrahydropyrimidine-2,4-dione (product of Example 4 of French patent No. 2,468,603 or compound B) was effected by repeating the test of Example 11 on oryza sativa with compounds A and B and the following results were found:

|  | Mortality percentage | | |
| Plant treated | Dose in kg/hectare | | |
| --- | --- | --- | --- |
| *Oryza Sativa* | 2.5 | 1.5 | 0.625 |
| Compound A | 0 | 0 | 0 |
| Compound B | 100 | 100 | 100 |

CONCLUSION

Compound A presents a total herbicidal selectivity on Oryza sativa, while compound B completely destroys the rice crop.

Various modifications of the compounds and method of the invention may be made without departing from the spirit or scope thereof and it is to be understood that the invention is intended to be limited only as defined in the appended claims.

What we claim is:

1. A compound which is 3-(2-tetrahydropyranyl)-1,2,3,4,6,7-hexahydro-1-p-tolyoxycarbonyl-5H-cyclopentapyrimidine-2,4-dione.

2. An herbicidal composition comprising an herbicidally effective amount of at least one compound of claim 1 and an inert carrier.

3. A method of selectively killing weeds comprising contacting weeds with and herbicidally effective amount of at least one compound of claim 1.

4. The method of claim 3 wherein the weeds are in a rice field.

5. The method of claim 3 wherein the weeds are in a cotton field.

6. The method of claim 3 wherein the weeds are in a corn field.

* * * * *